United States Patent [19]

Bagnall et al.

[11] 4,294,962

[45] Oct. 13, 1981

[54] CONTINUOUS PROCESS FOR THE MANUFACTURE OF CYANURIC ACID

[75] Inventors: Elizabeth A. Bagnall, Morrisville, Pa.; Basil A. Guiliano, Plainsboro; Henry A. Pfeffer, III, Mercerville, both of N.J.

[73] Assignee: FMC Corporation, Philadelphia, Pa.

[21] Appl. No.: 162,718

[22] Filed: Jun. 25, 1980

[51] Int. Cl.³ .......................................... C07D 251/32
[52] U.S. Cl. ..................................................... 544/192
[58] Field of Search ........................................ 544/192

[56] References Cited

U.S. PATENT DOCUMENTS

| | | | |
|---|---|---|---|
| 3,154,545 | 10/1964 | Symes et al. | 260/248 |
| 3,563,987 | 2/1971 | Berkowitz | 260/248 |
| 3,635,968 | 1/1972 | Goelz et al. | 260/248 |
| 3,954,751 | 5/1976 | Fuchs et al. | 260/248 |

*Primary Examiner*—John M. Ford
*Attorney, Agent, or Firm*—Robert W. Kell; Frank Ianno

[57] ABSTRACT

A highly-pure cyanuric acid is manufactured in a continuous process whereby urea and/or biuret are dissolved in an inert solvent and circulated at a high velocity and a temperature in the range of about 180° C. to about 250° C. through a loop between a heat exchanger and a forced circulation evaporative crystallizer body. Cyanuric acid crystallizes from the reaction mixture as it circulates to form a slurry. Ammonia formed during the reaction is removed at reduced pressure as the reaction mixture enters the evaporative crystallizer body. A portion of the slurry of cyanuric acid is continuously removed as it circulates through the loop and may be filtered to recover the cyanuric acid. The filtrate is returned to a feed tank and additional solvent, urea or biuret added to meet the concentration desired in the reaction mixture. The solution from the feed tank is added to the reaction mixture circulating through the loop at a rate to replace the volume of cyanuric acid slurry that is removed.

15 Claims, 3 Drawing Figures

CONTINUOUS PROCESS FOR THE MANUFACTURE OF CYANURIC ACID

This invention relates to a continuous process for the manufacture of cyanuric acid from urea and/or biuret by the pyrolysis of a solution of urea and/or biuret dissolved in an inert solvent.

It is known that cyanuric acid can be produced by the pyrolysis of urea. This reaction may be expressed by the equation:

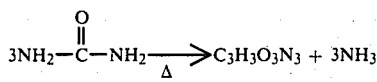

The resulting product, cyanuric acid, which has the empirical formula, $C_3H_3O_3N_3$, is generally represented structurally either as:

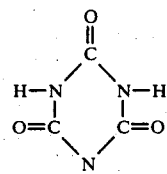

or

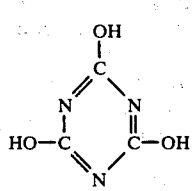

The pyrolysis can be carried out either in a dry state, that is, in the absence of a solvent, such as is described in U.S. Pat. No. 2,943,088, issued to R. H. Westfall on June 28, 1960, or in the presence of various organic solvents, such as described in U.S. Pat. No. 3,065,233, issued to Hopkins et al on Nov. 20, 1962; U.S. Pat. No. 3,117,968, issued to Merkel et al on Jan. 14, 1964; U.S. Pat. No. 3,164,591, issued to Walles et al on Jan. 5, 1976; or British Pat. No. 950,826, issued to Whiffen & Sons, Limited on Feb. 26, 1964.

Unfortunately, the pyrolysis of urea to cyanuric acid does not occur alone. A large range of products, in addition to cyanuric acid, is produced. These products may include the amino substituted cyanuric acids, commonly referred to as amides of cyanuric acid, namely ammelide, ammeline and melamine, as well as other undesirable by-products, such as ammonium carbamate, melam and other condensation products.

One major difficulty, therefore, in producing cyanuric acid by pyrolyzing urea or biuret is that vast numbers of by-products can be produced, and it is difficult to control the reaction so as to minimize the production of these undesired by-products. In addition, it is difficult to obtain the desired end product in good yield and in a purified form. High purity is especially important where the cyanuric acid is to be chlorinated, since it is essential, if safe chlorination and satisfactory chlorinated cyanuric acids are to be obtained, that a pure cyanuric acid be used as the raw material. Hence, it is necessary to obtain a commercial product essentially free of other pyrolytic degradation products of urea, and particularly of the amides of cyanuric acid, chiefly ammelide and ammeline.

In order to obtain a purified cyanuric acid, it is the custom in the art to treat crude cyanuric acid to an acid digestion. In this stage, the crude cyanuric acid is digested in a strong, acid bath, e.g., 3–15% sulfuric or hydrochloric acid. This acid treatment selectively hydrolyzes the acid-soluble, cyanuric acid amides, i.e., ammelide and ammeline, and converts them to cyanuric acid. In general, an acid digestion step is required where the concentration of ammelide or ammeline exceeds 1% by weight of the cyanuric acid product.

It is taught in U.S. Pat. No. 3,563,987, that cyanuric acid may be manufactured of such purity and freedom from cyanuric acid amides that acid digestion of the cyanuric acid product is not required if urea is heated in an inert solvent therefor at temperatures of 200° C.–250° C., under subatmospheric pressures. Sulfolane is suggested as a suitable solvent.

A continuous process for the manufacture of cyanuric acid is described in U.S. Pat. No. 3,954,751 wherein urea and an inert solvent are passed into a reaction zone in which pyrolysis of the urea to form cyanuric acid takes place at 200° C.–300° C. An externally heated tubular reactor or a thin layer reactor is employed to carry out the reaction. The ammonia formed in the reactor zone escapes from the liquid phase into the gas space provided by this type of reactor and passes with the vaporized solvent to a condensation zone from which the condensed solvent is returned to the reaction zone.

The cyanuric acid crystallizes from the reaction mixture in a crystal separation zone as a mash and is transferred to a falling film evaporator. The mash, containing crystallized cyanuric acid, is freed from solvent in the falling film evaporator and the solvent is returned to the reaction zone after condensation. One disadvantage of this process is that pluggage of the reactor tubes may occur, which could lead to the formation of hot spots, short circuiting and reduction in the rate of ammonia removal. In this process, the ammonia may be entrained in the reaction mixture for a substantial time before escaping to the gas space.

It is an object of the present invention to provide a process for the continuous production of cyanuric acid having a sufficient purity that the acid digestion step may be eliminated.

It is a further object of this invention to provide a continuous process for the pyrolysis of urea or biuret dissolved in an inert solvent whereby the ammonia that is formed upon pyrolysis of the reaction mixture is rapidly removed from the reaction mixture thereby reducing the formation of undesirable cyanuric acid amides.

In accordance with the present invention, a continuous process for the selected conversion of urea and/or biuret into cyanuric acid containing less than about 1% aminotriazines, is described. A reaction mixture comprising a solution of urea and/or biuret dissolved in an inert solvent is circulated at high velocity through a loop between a heat exchanger at substantially atmospheric pressure and a forced circulation evaporative crystallizer body at subatmospheric pressure that contains a moving reservoir of the reaction mixture at the bottom thereof. Sufficient heat is added to the reaction mixture as it passes through the heat exchanger to maintain the circulating reaction mixture at a temperature within the range of about 180° C. to about 250° C. and the heated reaction mixture from the heat exchanger enters the evaporative crystallizer body as a liquid stream below and preferably close to the surface level of the reservoir in the bottom section of the crystallizer. The liquid stream of reaction mixture is directed into the crystallizer in a manner to maximize agitation of the reaction mixture. The evaporative crystallizer body is maintained at a reduced pressure whereby ammonia gas is removed from the reaction mixture as it enters the crystallizer body and is withdrawn from the system.

The cyanuric acid formed by pyrolysis crystallizes from the reaction mixture and is circulated between the crystallizer body and heat exchanger as a slurry. A portion of this slurry of cyanuric acid suspended in the reaction mixture is removed as the reaction mixture circulates and pumped to a filter or centrifuge to separate the cyanuric acid product from the residual reaction mixture. The liquid reaction mixture that is separated in the filter or centrifuge, is pumped to a feed tank and sufficient inert solvent is added to make up any losses. Either urea or biuret is also added to the feed tank in the amount needed to make up the concentration of said compound in the reaction mixture as required. The freshly prepared reaction mixture from the feed tank is added to the reaction mixture circulating between the heat exchanger and evaporative crystallizer body at such a rate that the surface level in the evaporative crystallizer body is maintained at a desired level.

In carrying out the present invention, urea and/or biuret are dissolved in a suitable solvent. In order to be acceptable the solvent must be capable of dissolving urea or biuret in substantial quantities, and the final product, cyanuric acid, must be relatively insoluble therein. Additionally, the solvent must have a boiling point such that it does not boil at atmospheric pressure at the operating temperature of the process, i.e., 180° C.–250° C. Solvents that have been found effective are disclosed in U.S. Pat. No. 3,563,987. A particularly preferred solvent is sulfolane.

The continuous nature of the present process is extremely important in commercial manufacture as it substantially lowers the labor required and manufacturing costs.

The improved process of the present invention will be more apparent upon reference to the ensuing description and appended claims and drawings wherein:

Figure 1:
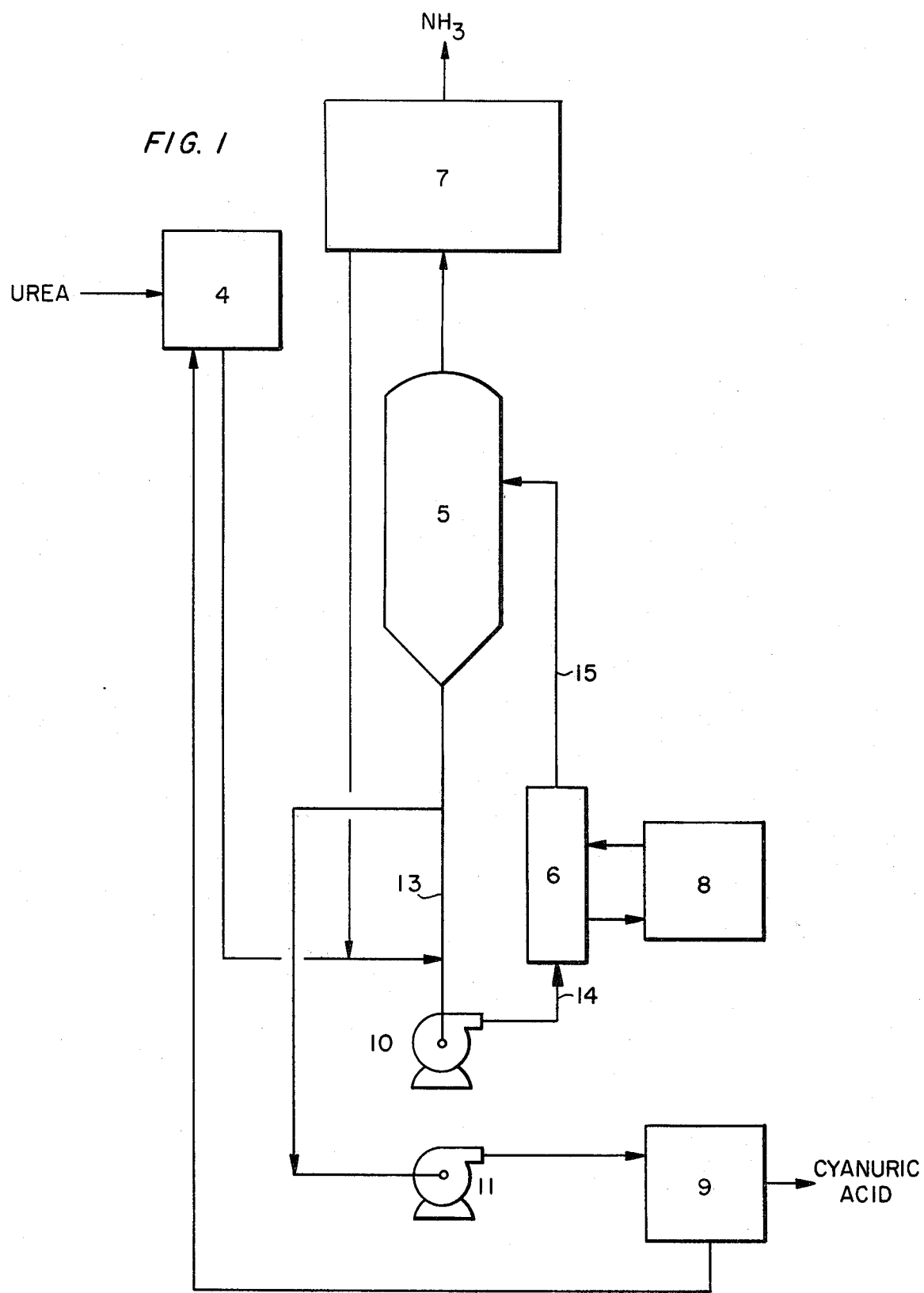
FIG. 1 is a flow diagram of the continuous process of the present invention.

Referring now to FIG. 1, the solution of urea and biuret may be made up in the desired solvent in a feed tank 4 that is external of the circulating loop formed by conduits 13, 14 and 15 between the heat exchanger 6 and crystallizer body 5. The temperature of the heat exchanger 6 is maintained by the heat source 8. The reaction mixture may be metered from the feed tank to the circulating reaction mixture at a rate which permits one to maintain the surface level of the liquid reservoir in the evaporative crystallizer body as desired. As stated above, the cyanuric acid will precipitate from the reaction mixture as it circulates to form a slurry, and the concentration of cyanuric acid in the circulating slurry may be varied by adjusting the concentration of urea and/or biuret in the feed solution. It has been found that concentrations between about 5 and about 40 weight percent urea in the solvent gives good results with concentrations of 30–35 weight percent being particularly preferred.

When the inert solvent used is sulfolane and the concentration of cyanuric acid in the slurry is about 5 to 30 weight percent the reaction mixture can be circulated rapidly by the pump 10 at a linear velocity of about 4 to 10 feet per second to maintain the cyanuric acid in suspension and provide sufficient agitation to assure that the temperature within the circulating reaction mixture is kept as uniform as possible. Circulation rates under 4 feet per second should be avoided as the cyanuric acid crystals will settle from suspension. Particularly preferred are circulation rates within the range of about 5 feet per second to about 10 feet per second. At these velocities, the entire volume of the reaction mixture is circulated from about once to about three times each minute.

The ammonia that is liberated during pyrolysis is removed from the reaction mixture as it enters the crystallizer which is maintained at a reduced pressure, preferably in the range of 0–400 mm Hg.

Figure 2:
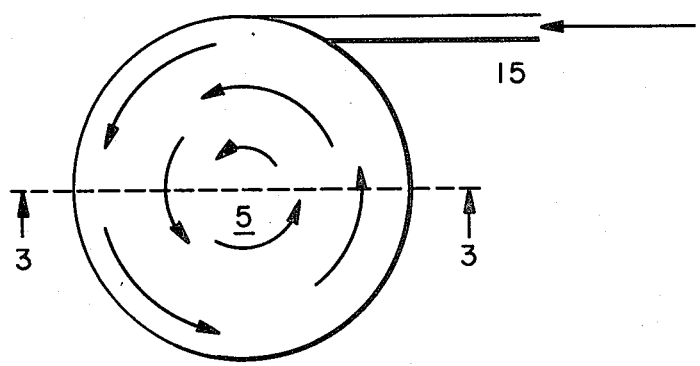
FIG. 2 is a sectional plan view of a forced circulating evaporative crystallizer body.
Figure 3:
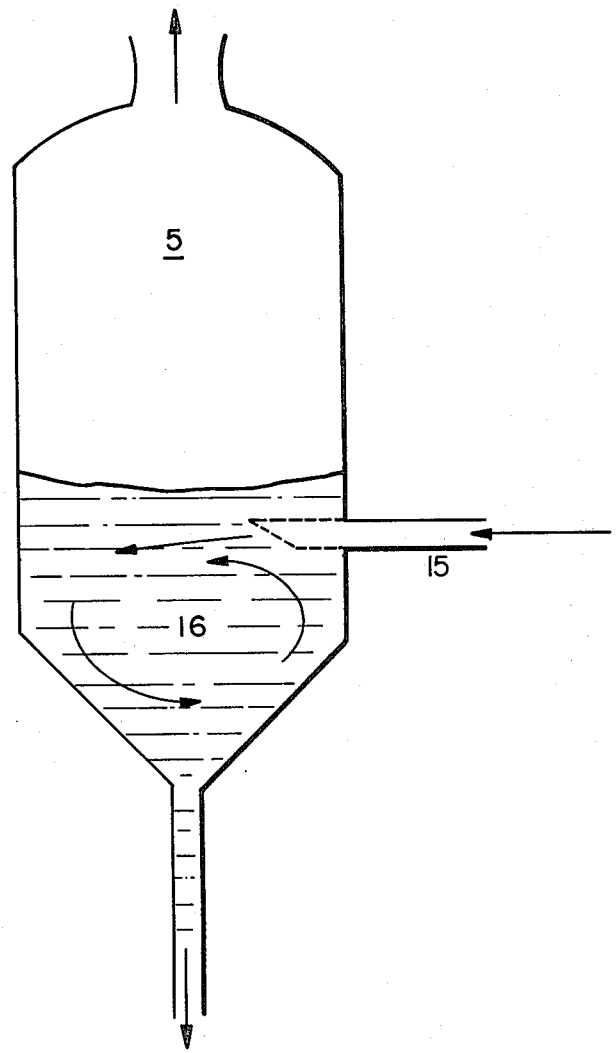
FIG. 3 is a section view of the crystallizer along the line 3—3 of FIG. 2.

Referring now to FIGS. 2 and 3, the liquid stream of the reaction mixture containing crystallized cyanuric acid in suspension enters the crystallizer body at a point that is below the surface level of the reservoir of reaction mixture 16. Preferably, the liquid stream will enter tangent to the cylindrical wall of the crystallizer body as shown in FIGS. 2 and 3 so as to form a turbulent vortex of slurry having sufficient surface area to permit the rapid disengagement of ammonia from the reaction mixture. The high velocity flow around the loop between the heat exchanger and the crystallizer body maintains the cyanuric acid in suspension and ensures that any ammonia which may be entrained in the reaction mixture will be subject to a reduced pressure of 150–400 mm Hg every minute.

Some of the inert solvent is vaporized as the reaction mixture enters the crystallizer. This volatilized solvent passes with the disengaged ammonia overhead to a condenser 7 where the solvent is condensed and returned to the crystallizer. The ammonia is vented from the condenser 7.

Both the circulating loop between the heat exchanger and crystallizer body, as well as the crystallizer body itself, are insulated. This combined with the rapid circulation of the reaction mixture through the heat exchanger reduces temperature fluctuation throughout the reaction mixture so that the pyrolysis reaction proceeds at a constant temperature ($\pm 2°$ C.) and uniform rate. When the reaction temperature is maintained within the range of about 180° C. to about 250° C. the total residence time of the reaction mixture is between one and four and preferably between one and three hours based on the volumetric feed rate. It is preferred for optimum performance of the process that the reaction temperature be within the range of about 200° C. to about 220° C., and that the pressure within the crystallizer body be maintained between about 200–250 mm Hg.

As shown in FIG. 1, the circulating slurry of cyanuric acid is continuously removed at a constant rate and is transferred by the pump 11 to a separation zone 9 where the crystalline cyanuric acid is separated (by filtration or centrifugation) from the liquid reaction mixture. The cyanuric acid product may be dried and the separated liquid reaction mixture containing 1% to 8% unreacted urea and/or biuret is returned to the feed tank 4. Urea and additional solvents, as required, are continuously added to the feed tank. The reaction mixture from the feed tank 4 is added to the circulating slurry of cyanuric acid at the same rate that the cyanuric acid slurry is removed to the separator zone.

In the following examples, set forth to further illustrate the present invention, all quantities are expressed in parts by weight unless otherwise indicated.

EXAMPLE I

A solution of 460 pounds of urea dissolved in 602 gallons of sulfolane (20 weight percent urea) flows from a feed tank 4 at the rate of 25 gallons per hour and is circulated between a heat exchanger 6 and forced circulation evaporative crystallizer body 5 at a rate such that the entire volume of the urea and/or biuret solution present in the crystallizer body passes through the heat exchanger twice each minute. The solution of urea enters the crystallizer body at a tangent to the cylindrical wall and beneath the surface of the liquid in the crystallizer, as is shown in FIGS. 2 and 3. The temperature of the circulating reaction mixture is maintained at 205° C. by the heat input as it passes through the heat exchanger and the pressure within the crystallizer body is 175 mm Hg.

Cyanuric acid precipitates from the reaction mixture as pyrolysis proceeds forming a slurry containing about 11% solids. This slurry is withdrawn as it circulates between the body of the crystallizer and the heat exchanger at the rate of 25 gallons per hour. The residence time of the reaction mixture within the circulating loop is 3 hours.

The cyanuric acid slurry withdrawn is pumped to a centrifuge 9 and the cyanuric acid separated by the centrifuge dried in a vacuum oven to give a product analyzing 0.55% aminotriazine. The yield based upon urea conversion is 86%.

The liquid reaction mixture from the centrifuge is returned to the feed tank 4. Urea and sulfolane are added to the feed tank as required to maintain the concentration of urea and/or biuret in the solvent at 20 weight percent. In a similar manner, biuret may be continuously pyrolyzed to form cyanuric acid.

EXAMPLES 2-12

In a series of 11 experiments, the continuous pyrolysis of urea is repeated as described in Example 1 above at reaction temperatures between 202° C. and 214° C. The pressure within the crystallizer is varied between 150 mm Hg and 245 mm Hg. The concentration of urea in the feed solution, residence time, amount of aminotriazine formed and conversion yields are given in Table I.

EXAMPLE 13

A laboratory scale version of the process described in Example I was performed with the temperature being held at 195° C. and the pressure above the liquid surface at 100 mm Hg. The concentration of urea in the feed was 30 weight percent. Cyanuric acid yields of 89% were obtained with a two hour residence time. In a similar manner, good yields of cyanuric acid may be obtained at 180° C. and 150 mm Hg by increasing the residence time to three hours.

EXAMPLE 14

The process described in Example I above may be repeated except that the temperature of the circulating reaction mixture is maintained at 220° C., and the pressure within the evaporative crystallizer body is maintained at 250 mm Hg. Cyanuric acid may be isolated in good yield as a white crystalline solid of large particle size (94% retained on a 200 U.S. mesh screen, i.e., 74 microns).

TABLE I

PROCESS CONDITIONS & STEADY STATE RESULTS

| Run No. | Temp. (°C.) | Pressure (mm Hg) | Time (hr) | Feed % Urea | Volume (gal) | % Aminotriazine CA Basis | % Conversion (one pass) |
|---|---|---|---|---|---|---|---|
| 2 | 202 | 170 | 3 | 30 | 75 | 0.45 | 83.0 |
| 3 | 208 | 150 | 3 | 20 | 75 | 0.30 | 87.0 |
| 4 | 214 | 175 | 3 | 30 | 50 | 0.45 | 92.0 |
| 5 | 207 | 172 | 2 | 30 | 50 | 0.47 | ~83.0 |
| 6 | 205 | 170 | 2 | 20 | 75 | 0.16 | ~84.0 |
| 7 | 208 | 168 | 3 | 20 | 75 | 0.20 | 88.0 |
| 8 | 206 | 170 | 3 | 30 | 75 | 0.24 | 86.5 |
| 9 | 210 | 200 | 3 | 30 | 75 | 0.30 | 88.0 |
| 10 | 208 | 200 | 3 | 35 | 75 | NA | 88.0 |
| 11 | 208 | 200 | 3 | 40 | 75 | 0.56 | 88.0 |
| 12 | 210 | 245 | 3 | 35 | 75 | 0.35 | 90.0 |

We claim:
1. A continuous process for the manufacture of a substantially pure cyanuric acid by pyrolysis of a compound selected from the group consisting of urea and biuret dissolved in an inert solvent which comprises the steps of:
   (a) circulating, at high velocity a reaction mixture comprising a solution of a compound selected from the group consisting of urea and biuret dissolved in an inert solvent through a loop between a heat exchanger and a forced circulation evaporative crystallizer body that contains a reservoir of the reaction mixture at the bottom thereof;
   (b) introducing the circulating reaction mixture into the evaporative crystallizer body below the surface level of said reservoir in a manner to maximize the surface area of the reaction mixture as it enters the crystallizer;
   (c) adding sufficient heat at the heat exchanger to maintain the circulating reaction mixture at a temperature within the range of about 180° C. to about 250° C.;
   (d) crystallizing cyanuric acid from the reaction mixture as it circulates between the heat exchanger and the evaporative crystallizer body to form a slurry of cyanuric acid crystals;
   (e) removing ammonia at a reduced pressure from the reaction mixture in the evaporative crystallizer body;
   (f) removing a portion of the slurry of cyanuric acid crystals and the reaction mixture as it circulates;
   (g) separating cyanuric acid crystals from said reaction mixture;
   (h) returning the separated reaction mixture in the preceeding step to a feed tank;
   (i) adding a compound selected from the group consisting of urea and biuret and an inert solvent to said feed tank to maintain the desired concentration of said compound in the reaction mixture, and
   (j) adding the reaction mixture from the feed tank to the circulating reaction mixture to maintain the desired surface level in the evaporative crystallizer body.

2. The process of claim 1 wherein the circulating reaction mixture is maintained at a constant temperature ±2° C.

3. The process of claim 2 wherein the circulating reaction mixture is maintained within the range of about 200° C. to about 220° C.

4. The process of claim 1 wherein said inert solvent is sulfolane.

5. The process of claim 1 wherein said loop between the heat exchanger and crystallizer is insulated.

6. The process of claim 1 wherein said evaporative crystallizer is insulated.

7. The process of claim 1 wherein the cyanuric acid crystals are present throughout the reaction mixture.

8. The process of claim 1 wherein said circulating reaction mixture impinges tangentially against the internal wall of the evaporative crystallizer as it enters thereby increasing the surface area of the reaction mixture and facilitating the removal of ammonia.

9. The process of claim 1 wherein the pressure within the evaporative crystallizer is from about 150 to about 250 mm Hg.

10. The process of claim 8 wherein said heat exchanger is maintained at substantially atmospheric pressure.

11. The process of claim 1 wherein the hydraulic residence time of the circulating reaction mixture is from about 1 to about 4 hours.

12. The process of claim 1 wherein the velocity of the circulating reaction mixture is such that it flows between the heat exchanger and crystallizer from about once to about twice each minute.

13. The process of claim 1 wherein said compound is urea.

14. The process of claim 1 wherein said compound is biuret.

15. Apparatus for the continuous manufacture of crystalline cyanuric acid comprising in combination, a feed tank, a forced circulation evaporative crystallizer body, and a heat exchanger; means for recirculating a reaction mixture containing a compound selected from the group consisting of urea and biuret dissolved in an inert solvent and heated to an elevated temperature, through a loop between said crystallizer body and said heat exchanger while maintaining the temperature of said reaction mixture in the range of about 180° C. to about 220° C.; means for applying a vacuum to said crystallizer body and removing ammonia from the reaction mixture as it enters the crystallizer body; means for continuously withdrawing a portion of the reaction mixture containing crystalline cyanuric acid as it is circulated; means for separating the reaction mixture that is withdrawn from said cyanuric acid associated therewith; means for returning the separated reaction mixture from the preceeding step to the feed tank; means for adding said compound and an inert solvent to the feed tank; and means for adding reaction mixture from the feed tank to the reaction mixture that is circulating through said loop.

* * * * *